United States Patent
Mukhopadhyay et al.

(10) Patent No.: US 10,046,079 B2
(45) Date of Patent: Aug. 14, 2018

(54) CLAY COMPOSITES AND THEIR APPLICATIONS

(71) Applicant: Materials Modification Inc, Fairfax, VA (US)

(72) Inventors: Kausik Mukhopadhyay, College Park, MD (US); Krishnaswamy Kasthuri Rangan, Fairfax, VA (US); Tirumalai Srinivas Sudarshan, Vienna, VA (US)

(73) Assignee: MATERIALS MODIFICATION INC.

( * ) Notice: Subject to any disclaimer, the term of this patent is extended or adjusted under 35 U.S.C. 154(b) by 374 days.

(21) Appl. No.: 14/210,082

(22) Filed: Mar. 13, 2014

(65) Prior Publication Data

US 2014/0276484 A1 Sep. 18, 2014

Related U.S. Application Data (60) Provisional application No. 61/794,420, filed on Mar. 15, 2013.

(51) Int. Cl.
    *A61L 15/18* (2006.01)
    *A61L 15/44* (2006.01)
    *A61L 15/46* (2006.01)

(52) U.S. Cl.
    CPC .............. *A61L 15/18* (2013.01); *A61L 15/44* (2013.01); *A61L 15/46* (2013.01); *A61L 2300/402* (2013.01); *A61L 2300/404* (2013.01)

(58) Field of Classification Search
None
See application file for complete search history.

(56) References Cited

U.S. PATENT DOCUMENTS

| | | |
|---|---|---|
| 3,761,590 A | 9/1973 | Fox, Jr. |
| 4,020,150 A | 4/1977 | Wysor |
| 4,049,802 A | 9/1977 | Fox, Jr. |
| 4,078,058 A | 3/1978 | Fox, Jr. |
| 4,088,754 A | 5/1978 | Monafo |
| 4,254,104 A | 3/1981 | Suzuki |
| 4,384,117 A | 5/1983 | Wysor |
| 4,393,048 A | 7/1983 | Mason, Jr. |
| 4,404,197 A | 9/1983 | Fox, Jr. |
| 4,446,124 A | 5/1984 | Fox, Jr. |
| 4,551,139 A | 11/1985 | Plaas |
| 4,559,223 A | 12/1985 | Fox, Jr. |
| 4,581,028 A | 4/1986 | Fox, Jr. |
| 4,599,226 A | 7/1986 | Fox, Jr. |
| 4,769,078 A * | 9/1988 | Tso .......................... C01B 33/44 106/287.25 |
| 4,952,411 A | 8/1990 | Fox, Jr. |
| 5,143,717 A | 9/1992 | Davis |
| 5,330,980 A | 7/1994 | Shin |
| 5,334,588 A | 8/1994 | Fox, Jr. |
| 5,374,432 A | 12/1994 | Fox, Jr. |
| 5,480,717 A | 1/1996 | Kundel |
| 5,653,994 A | 8/1997 | Schneider |
| 5,744,151 A | 4/1998 | Capelli |
| 5,753,269 A | 5/1998 | Groh |
| 5,785,972 A | 7/1998 | Tyler |
| 5,817,322 A | 10/1998 | Xu |
| 6,015,816 A | 1/2000 | Kostyniak |
| 6,093,414 A | 7/2000 | Capelli |
| 6,551,577 B1 | 4/2003 | Chen |
| 6,716,895 B1 | 4/2004 | Terry |
| 7,011,839 B2 | 3/2006 | Ciszewski |
| 7,179,849 B2 | 2/2007 | Terry |
| 7,285,576 B2 | 10/2007 | Hyde |
| 7,520,923 B2 | 4/2009 | Marcoon |
| 7,744,681 B2 | 6/2010 | Marcoon |
| 7,745,509 B2 | 6/2010 | Burton |
| 7,820,284 B2 | 10/2010 | Terry |
| 8,034,454 B2 | 10/2011 | Terry |
| 8,192,764 B2 | 6/2012 | Burton |
| 8,193,267 B2 | 6/2012 | Burton |
| 8,231,883 B2 | 7/2012 | Sugiura |
| 8,308,841 B2 | 11/2012 | Yamaji |
| 8,343,403 B2 | 1/2013 | Gavalas |
| 2003/0170295 A1* | 9/2003 | Kim ..................... A61K 9/7061 424/449 |
| 2009/0202806 A1 | 8/2009 | Ebina |
| 2012/0183588 A1 | 7/2012 | Supamahitorn |

FOREIGN PATENT DOCUMENTS

| | | |
|---|---|---|
| EP | 1747723 | 1/2007 |
| WO | 94/20074 | 9/1994 |

OTHER PUBLICATIONS

Brett, DW, A Review of Moisture-Control Dressings in Wound care, J. Wound Ostomy Continence Nurs., 33(6S):S3-S8 (2006).
Renz, EM, Canclo, LC, Barillo, DJ, White, CE, Albrecht, MC, Thompson, CK, Ennis, JL, Wanek, SM, King, JA, Chung, KK, Wolf, SE, and, Holcomb, Col JB, Long, Range Transport of War-Related Burn Casualties, Journal of Trauma, Injury, Infection, and Critical Care, 64:S136-S145 (2008).
Tarantino,DP, Burn Pain and Dressing Changes, Techniques in Regional Anesthesia and Pain Management, 6(1):33-38, (2002).
Sondi, I and Salopek-Sondi, B, Silver Nanoparticles as Antimicrobial Agent: a case study on *E-coli* as a model for Grame-negative bacteria, Journal of Colloid and Interface Science, 275:177-182 (2004).
Aguzzi, C, Cerezo, P, Viceras, C and Caramella, C, Use of clays as drug delivery systems: Possibilities and Limitations, Applied Clay Science, 36:22-36(2007), Elsevier B.V.
Carretero, MI, Clay minerals and their beneficial effect upon human health. A review, Applied Clay Science, 21:155-163(2002), Elsevier Science B.V.
Kevadiya, BD, Joshi, GV, Patel, HA., Ingole, PG, Mody, NM, and, Bajaj, HC, Montmorillonite-alginate Nanocomposites as a Drug Delivery System: Intercalation and In Vitro Release of Vitamin B1 and Vitamin B6, Journal of Biomaterials Applications, 25: 161-177 (2010).
One (1) page of International Search Report dated Jul. 17, 2014 in International Appl Ser. No. PCT/US2014/027388.

\* cited by examiner

*Primary Examiner* — Jessica Worsham
(74) *Attorney, Agent, or Firm* — Jyoti C. Iyer (57) ABSTRACT

Clay composite sheets, mats, films or membranes without polymers. Methods of preparing clay composite sheets, mats, films or membranes without using polymers in the method. Methods of using clay composite sheets, mats, films or membranes prepared without using polymers. Antimicrobial dressing having organo-modified clay product. Transdermal delivery of drugs using organo-modified clay product and methods.

11 Claims, 6 Drawing Sheets

CLAY COMPOSITES AND THEIR APPLICATIONS

RELATED APPLICATIONS

This application claims benefit of U.S./PCT Application Ser. No. 61/794,420 filed Mar. 15, 2013, which is incorporated in its entirety by reference.

FIELD

This disclosure relates to clay composites sheets and films prepared without adding polymer additives.

This disclosure provides methods of preparing clay composite sheets and their applications such as for antimicrobial wound dressing, flame retardants, solvent separation membrane, and drug delivery.

BACKGROUND

In this section, we discuss several aspects of related work, including background and conventional technologies.

Clays

Clay is an aluminosilicate, which has a layered sheet-like structure with silica tetrahedral bonded to alumina octahedral in different ratios through Van der Waal's forces. Types of clay with a 2:1 ratio of tetrahedral to octahedral are known as smectite clays. A common type of smectite clay is Montmorillonite (MMT).

Clays are common ingredients in pharmaceutical products. Clay minerals are naturally occurring inorganic cationic exchangers and so they can undergo ion exchange with basic drugs in solution. In addition to ion-exchange, organic molecules can bond to clays via physical adsorption and ion-dipole interactions of acidic and non-ionized molecules. For example. Wai and Banker demonstrated the loading of alkaloids in montmorillonite clay.

Medicinal and therapeutic applications of various clays and their products have long been used for the treatment of skin ailments. Montmorillonite (MMT) is one of the most widely used medicinal clays. Studies have shown that MMT is non-toxic and thus has no side effects. Montmorillonite and its products have a broad spectrum of applications in medicine for cleansing and protection of skin, antibacterial activity and blood clotting capabilities. Clay can also accelerate healing in simple wounds.

MMT has also been used in the delivery of vitamins such as thiamine hydrochloride (Vitamin B1; VB1) and pyridoxine hydrochloride (Vitamin B6; VB6) to the intestinal environment. The controlled release of VB1/VB6 was observed.

Another major advantage of using clays to deliver drugs is the very low risk of 'dose dumping'. Dose dumping is an unexpected sudden release of the entire dose, which may cause severe or even lethal side effects because of the narrow therapeutic window of high potency drugs. Common topical medical dressings such as gauze, membranes and textiles can be subjected to dose dumping easily due to external forces such as temperature change, pH change, and enzyme activity. Thus, a material of high chemical and mechanical resistance is required to develop a safe, high potency opioid transdermal drug delivery vehicle. Clays are the most optimum materials for storage and delivery systems for drugs such as analgesics because of the mechanical and chemical stability of clay. For example, Fentanyl has been loaded into a metakaolin clay, which provided a mechanically strong sustained drug release medium.

Typically, clay particles are dispersed in aqueous drug solutions, dispersions are allowed to equilibrate for a suitable time, and finally solid particulates are recovered and dried. Clay in the particulate form (powders) are not suitable for use in preparing topical wound dressing or for transdermal application of drugs because these methods require a continuous film so that drugs can diffuse without interruption from the dressing. In the case of clay particles there does not exist a continuous path for drugs to diffuse from the clay particles to wound or skin surface. Clays in the form of thin sheets are preferable for topical wound dressing and transdermal drug delivery applications.

Clay sheets made using polymer binders which are commonly known as 'polymer-clay composites' are available in the market. In these polymer-clay composites, the polymers act as a medium to disperse clay particles and to provide mechanical stability to the polymer-clay composite sheets. The clay nanocomposite of various polymeric materials such as polystyrene, nylon-6, polyaniline, polymethyl methacrylate (PMMA), polyurethane, polyethylene, poly (styrene-co-acrylonitrile), polyaniline, polypyrrole, polysulfone, polyacrylates, polyimide and epoxy have been investigated for a variety of applications.

The initial question that arose was how to create a clay film that does not fall apart and does not make use of significantly large polymers. It is preferable to have clay sheets without any polymer additives in certain applications where polymer additives can hinder or reduce the permeation of moisture, or chemicals or drugs though the clay sheets. It is also preferable to have a continuous sheet clay uninterrupted by the polymer matrix. In this way special properties of clay particles such as adsorption, permeability, high temperature stability, ion-exchange property, hemostasis property, and wound healing property can be fully utilized without being disturbed by the properties of polymer additives.

Antimicrobial Burn Wound Dressing

Antimicrobial silver-nylon dressing product known in the prior art prevents infection at a surgical site, enhances negative pressure therapy and help treat burns and wounds. These dressings have a permanently plated metallic surface. They continuously deliver a flow of silver ions into the wound, can be used for up to 7 days, do not increase the number of contaminating microbes before sterilization and do not stain.

Another prior art product contains two layers of silver-coated polyethylene mesh, enclosing a layer of rayon and polyester. The silver is put on the polyethylene mesh in a vapor deposition process. This process leads to the formation of nanocrystals of the metallic silver which help fight against the various gram positive and negative bacteria. This product is mainly used as a barrier layer for burns and donor sites. The difference between these products and this disclosure is that these products release silver into the wounded area to tight the microbes. The silver ions in this disclosure are contained within the clay film.

Transdermal Drug Delivery

Burns are among the most painful and debilitating battlefield wounds faced by the US warfighter. Burn wounds turn deadly when infection sets in. Since military operations began in Iraq in March 2003, hundreds of US military personnel have sustained burn injuries from explosions and other implements of war such as IED's. Not only is acute burn injury pain a source of immense suffering, but it has been linked to debilitating chronic pain and stress-related disorders. Severe pain is felt during acute treatment and rehabilitation, especially during dressing changes, debridement's, and skin grafting, and continues through long-term follow up. The backbone of burn analgesia is opioid therapy, typically administered via oral or parenteral routes. The use of opioid medications in burn patients is complicated by the side effects such as tolerance, hyperalgesia, hemodynamic instability, respiratory depression, and dependence. Therefore, beside the systemic administration of analgesics, attempts have been made to control the pain locally using topical analgesics which has shown encouraging results. Such topical dressings can be used to protect the burn wound from infection and thereby aid in wound healing if an antimicrobial property can be imparted onto them.

Treatment for reducing the pain involves the usage of common and opioid analgesics, nonsteroidal anti-inflammatory drugs (NSAIDs) and adjuvant analgesics. Pharmacologically, it is known that the main mechanism of action of analgesics is to act at specific sites located in the CNS and periphery. This observation led topical administration of pain reliever drugs such as NSAID's, local anesthetics, capsaicin, tricyclic antidepressants, ketamine, clonidine, opioids, and cannabinoids. For example, fentanyl transdermal patches are used in chronic pain such as cancer pain or in the post-operative setting. The topical application of these drugs allows high concentrations in peripheral effector sites. Thus, undesirable side effects are less likely to occur compared to delivering these drugs systemically. Even though opioid drugs are applied locally on the skin, the main analgesic action of opioids occurs only in the spinal cord. This will require the drug to be absorbed into the blood and travel from the skin surface to the spinal cord.

Local anesthetic creams have been used in burn wound dressings. For example, Lidocaine prilocalne cream has been used as a topical anesthetic by physicians performing plastic surgery and in patients with face burn injury. Topical application of loperamide also reduced the pain in full-thickness burn wounds by acting on the peripheral nociceptors. Therefore, a combination of local anesthetics such as lidocaine and opioid drugs such as fentanyl may be incorporated in to the clay sheets and can be used in transdermal pain medication.

Separation Membrane

The United States must develop and deploy clean, affordable, domestic energy sources as quickly as possible to achieve energy security and independence. Batteries power everything from tools to cars to remote controls and have a major role in our daily lives. There is an increasing interest in the energy efficient production of Dimethyl Carbonate (DMC) that will support a growing market for hybrids and electric vehicles, and significantly reduce our dependence on foreign oil as well as correspondingly reduce greenhouse gas emissions.

Dimethyl carbonate is used as a substitute for toxic products such as phosgene as well as traditional methylation agents. Other applications include as a solvent for coatings, an octane booster in petrol, and as a component of diesel. In the last decade DMC has shown immense promise as an electrolyte solvent for lithium battery applications due to its inherent safety and robustness. Despite the enormous promise of its industrial use, this chemical is currently entirely imported from China and Japan. Recently, South Korea has entered into the global DMC production foray. Other global chemical industries include EniChem (Italy), Bayer (Germany) and Catalytic Distillation Technologies (Netherlands), and to a certain extent, BASF (Germany).

Carbon dioxide conversion to DMC is a very challenging and sensitive reaction, because of the high Carbon dioxide activation energy required to convert Carbon dioxide and methanol. Most reports concentrate on gas phase reaction and conversion of carbon dioxide to DMC with 3.5% yield.

One of the critical problems of catalytic direct synthesis of DMC is the co-generation of water, which causes hydrolysis of the DMC formed during the reaction. It is thus important to remove the water generated during the reaction.

OBJECTS AND SUMMARY OF INVENTION

The disclosure provides a polymer-free organo-modified clay product. The clay product has a clay and an organic compound. The organo-modified clay product is a film, a sheet, a mat or a membrane. The disclosed organo-modified clay product is referred to as polymer-free because polymer is not added for preparation of the clay product. The clay is montmorillonite, kaolinite, smectite, and bentonite. The organic compound is betaine, betaine hydrochloride, choline chloride, 3-Benzyl-5-(2-hydroxymethyl)-4-methylthiazolium chloride, 3-Benzyl-5-(2-hydroxymethyl)-4-methylthiazolium bromide, 3-Benzyl-5-(2-hydroxymethyl)-4-methylthiazolium fluoride or 3-Benzyl-5-(2-hydroxymethyl)-4-methylthiazolium iodide.

In some embodiments, a thickness of the polymer-free organo-modified clay product ranges from about 1 micrometer to about 500 micrometer. In some embodiments, a thickness of the polymer-free organo-modified clay product ranges from about 1 micrometer to about 100 micrometer. In some embodiments, a thickness of the polymer-free organo-modified clay product ranges from about 20 micrometer to about 60 micrometer. In some embodiments, a thickness of the polymer-free organo-modified clay product is about 50 micrometer.

In some embodiments, the polymer-free organo-modified clay product achieves a bending radius of curvature ranging from about 0.4 millimeter to about 10 centimeter. The bending radius of curvature is achieved without breaking the polymer-free organo-modified clay product. In some embodiments, the polymer-free organo-modified clay product achieves a bending radius of curvature ranging from about 0.3 millimeter to about 10 millimeter. In some embodiments, the polymer-free organo-modified clay product achieves a bending radius of curvature of about 0.5 millimeter. In some embodiments, the polymer-free organo-modified clay product achieves a bending radius of curvature of about 0.4 millimeter.

In some embodiments, the polymer-free organo-modified clay product has greater than 50% absorption of visible light. In some embodiments, the polymer-free organo-modified clay product is non-transparent. In some embodiments of the polymer-free organo-modified clay product, when the thickness of the product was about 50 micrometer, the film had greater than 50% absorption of visible light. In some embodiments, when the organo-modified clay product was further modified by addition of silver, the film absorbed greater than 82% of the visible light.

In some embodiments, the polymer-free organo-modified clay product does not incorporate a polymer. In some embodiments, the organo-modified clay product is a polymer free composite.

In some embodiments, the polymer-free organo-modified clay product includes an antimicrobial agent. The antimicrobial agent can be silver ion, copper, iodine, proflavine, silver-containing compounds, copper containing compounds, quarternary ammonium compounds, or quarternary phosphonium compounds. Silver-containing compounds include but not limited to silver sulfadiazine, silver nitrate, silver oxide, and silver carbonate; copper containing compounds include but not limited to copper oxide, copper sulfate, copper acetate, and copper nitrate; quarternary ammonium compounds include but not limited to benzalkonium alkyl chloride, cethyl trialkyl ammonium chloride, and alkyl dimethyl benzyl ammonium chloride and quarternary phosphonium compounds include but not limited to alkyl trimethyl phosphonium chloride and dialkyl dimethyl phosphonium bromide.

In some embodiments, the polymer-free organo-modified clay product includes an analgesic. The analgesic can be opioid analgesics, nonsteroidal anti-inflammatory drugs (NSAIDs) and adjuvant analgesics, capsaicin, clonidine, ketamine, Morphine, fentanyl, Buprenorphine or cannabinoids.

Some embodiments provide an antimicrobial dressing having the polymer-free organo-modified clay product. Some embodiments provide a burn wound dressing having the polymer-free organo-modified clay product.

Some embodiments provide a lithium battery having the polymer-free organo-modified clay product. The organo-modified clay product is the electrolyte membrane in the lithium battery.

Some embodiments provide a flame retardant product having the polymer-free organo-modified clay product. In some embodiments, the flame retardant product resists breakdown following ethylene flame for 2 minutes.

Some embodiments provide a method of antimicrobial treatment by administering the polymer-free organo-modified clay product.

Some embodiments provide a method of treating burns by administering the polymer-free organo-modified clay product.

Some embodiments provide a method of removing water from organic chemical mixtures using the polymer-free organo-modified clay product.

Some embodiments provide a method of preparing a polymer-free organo-modified clay product. The method includes mixing a clay particle and an organo-containing solution to form a slurry. 'Organo-containing solution' can be defined as 'an organic chemical dissolved in a solvent including but not limited to water and ethanol'. Then the slurry is cast on a substrate to obtain a slurry cast. Then the slurry cast is dried to obtain a dried product of the slurry on the substrate. Then the dried slurry product is separated from the substrate. The separated dried slurry product is the polymer-free organo-modified clay product. The polymer-free organo-modified clay product can be a film, a sheet, a mat or a membrane. In some embodiments, if the substrate is glass, then the dried slurry product has to be removed from glass substrate. In some embodiments, if the substrate is fabric or nylon, the dried slurry product need not be removed from the fabric or nylon. The resulting dried slurry product on the fabric or nylon substrate can together form part of a wound dressing product. Thus, dried slurry need not be removed from a nylon or fabric substrate. In this disclosed methods, no polymer has been added to the clay for preparing the product. In some embodiments of the method, the substrate can be a silicone sheet, a fabric, or a glass surface. In some embodiments, the fabric is nylon. In some embodiments of the method when the product is prepared at a temperature of about 25° C., the viscosity of the slurry prepared for spreading on the substrate ranges from about 2 centipoise to about 20 centipoise. In some embodiments of the method when the product is prepared at a temperature of about 25° C., the viscosity of the slurry prepared for spreading on the substrate ranges from about 5 centipoise to about 10 centipoise. In some embodiments drying the slurry casted on the substrate is performed under conditions of slow, air. In some embodiments drying the slurry casted on the substrate is performed at 20-25 degrees Centigrade under ambient, room temperature conditions.

Some embodiments provide a method of preparing a polymer-free organo-modified clay product. The method includes mixing a clay particle and an organo-containing solution to form a slurry. Then the slurry is casted on a substrate to form a slurry casted on a substrate product. Then the slurry casted on the substrate is dried to obtain the polymer-free organo-modified clay product. The organo-modified clay product can be a film, a sheet, a mat or a membrane.

Some embodiments provide a method of preparing a polymer-free organo-modified clay product having an antimicrobial agent. The method includes mixing a clay particle and an organo-containing solution. Then an antimicrobial agent containing solution is added to obtain a slurry. The slurry is casted onto a substrate. The casted slurry and substrate are subjected to drying and a dried slurry is obtained on the substrate. The dried slurry is separated from the substrate to obtain the organo-modified clay product containing the antimicrobial agent.

Some embodiments provide a method of preparing a polymer-free organo-modified clay product having an analgesic. The method includes mixing a clay particle and an organo-containing solution. Then an analgesic containing solution is added and a slurry is obtained. The slurry is casted on a substrate and dried to obtain a dried slurry on the substrate. The dried slurry is separated from the substrate to obtain the polymer-free organo-modified clay product having the analgesic compound.

Some embodiments provide an antimicrobial wound dressing. The wound dressing has a polymer-free organo-modified clay product having an antimicrobial agent. The wound dressing has successive layers of the following: a hydrogel adhesive with a hydrophobic backing; a polymer-free organo-modified clay product having an antimicrobial agent; and, a nylon membrane.

Some embodiments provide a method of preparing an antimicrobial wound dressing. The method includes successively layering the following: a hydrogel adhesive with a hydrophobic backing; a polymer-free organo-modified clay product having an antimicrobial agent; and, a nylon membrane. In some embodiments, the method includes successively layering the following: a nylon membrane, then a polymer-free organo-modified clay product having an antimicrobial agent; and, then a hydrogel adhesive with a hydrophobic backing.

Some embodiments provide an analgesic wound dressing. The analgesic wound dressing includes a polymer-free organo-modified clay product having an analgesic. The wound dressing has successive layers of the following: a hydrogel adhesive with a hydrophobic backing; a polymer-free organo-modified clay product having an analgesic and, a nylon membrane. Some embodiments provide a transdermal wound dressing. Some embodiments provide a method of preparing a transdermal wound dressing.

Some embodiments provide a method of preparing an analgesic wound dressing. The method includes successively layering the following: a hydrogel adhesive with a hydrophobic backing; then a polymer-free organo-modified clay product having an analgesic and, then a nylon membrane. Alternatively, the successive layering can be as follows: nylon membrane, then a polymer-free organo-modified clay product having an analgesic followed by a hydrogel adhesive with a hydrophobic backing.

BRIEF DESCRIPTION OF THE DRAWINGS

The above objectives and advantages of the disclosed teachings will become more apparent by describing in detail preferred embodiments thereof with reference to the attached drawings in which.

DETAILED DESCRIPTION

Clay Films or Sheets

The disclosure relates to preparation, properties and applications of thin clay sheets.

Montmorillonite clay has excellent adsorbent as well as particle clumping properties. Cations such as sodium, lithium, and potassium reside in the gap between these layers known as the gallery or the interlayer. The gallery allows for 3 processes to occur: hydrophobic modification, intercalation and exfoliation.

Intercalation is when an organic component is inserted in between the gallery, causing expansion, yet still maintaining a well-defined spatial relationship between the layers. Intercalation causes the gallery to expand up to 1 to 2 angstrom. Exfoliation is a delaminating process where the gallery expands to the point where the layers completely separate from each other. This is accomplished through the adsorption of desired molecules. During exfoliation, packets of clay platelets separate from one another. Platelets at the outermost region of each packet cleave off, exposing more platelets for separation. The gallery expands up to 20 to 30 angstrom in the case of exfoliation, almost 20 times more than intercalation.

The initial question that arose was how to create a clay film that does not fall apart and does not make use of significantly large polymers. Montmorillonite clay naturally forms stacks of plate-like structures called platelets, with each platelet being less than 10 angstrom thick. The gallery spaces between the platelets can be filled with monomers, oligomers, or polymers to increase the distance between the platelets. The clay must expand but not enough to lose its stack organization because if it becomes exfoliated, it will fail to form an intact film.

In some embodiments organo-modified clay sheet made by using zwitter ions (ionic compounds containing both positive and negative ions in the same molecule) such as Betaine, Betaine hydrochloride, Choline chloride, 3-Benzyl-5-(2-hydroxymethyl)-4-methylthiazolium chloride and bromide, chloride, fluoride and iodide salts of tetraheptylammonium and cetyltrimethylammonium cations; all of them having a very high charge density to intercalate the clay layer intergallery.

Solvents that can be used for making the clay and organo-modified clay may include water, alcohols, organic solvents such as toluene, dimethyl formamide, dimethyl carbonate, chloroform, and acetonitrile. The drying times required for formation of clay and organo-modified films ranges from about 0 to about 24 days. In some embodiments, the drying time ranges from about 1 minute to about 24 hours. In some embodiments, the drying time ranges from about 5 to about 12 hours. The curing can be accelerated by heating using a microwave, or Ultra Violet radiation or Infrared radiation or conventional heat source. Low humidity can also accelerate the curing.

The disclosed teachings provide preparation of clay in the form of thin film, cut into desirable sizes.

The disclosure provides fabrication of a clay film covered with mesh and put onto the adhesive material that serves as the base of the bandage.

Some embodiments use clay film in a wound dressing. Some embodiments use clay film in a burn wound dressing. Some embodiments use clay film in an antimicrobial dressing for gram negative and gram positive bacteria. Some embodiments use clay film in a hemostatic dressing.

Some embodiments use clay film as a packaging material.

Some embodiments use clay film as a permeable, semi-permeable and non-permeable membrane.

Some embodiments use clay film self-extinguishing membrane and film.

The disclosure relates to synthesis of organo-modified clay films that can be incorporated with metal and non-metallic cations and able to make small to large dimension free standing clay films and membranes upon drying.

Some embodiments use clay film as a fire retardant barrier film.

Some embodiments prepare clay sheets without using binders and polymers.

Some embodiments use clay sheets as a separation membranes for oil-water, organic molecules-water, organic molecules-organic molecules, polar-polar, nonpolar-nonpolar, polar-nonpolar, metals-solutions, minerals-solutions, pollutants and non-pollutants Some embodiments use clay film as a UV-resistant, IR-resistant, hydrophobic and hydrophilic coating materials Some embodiments use metal exchanged organo modified clay films for energy storage devices such as batteries, capacitors, supercapacitors etc.

Organomodified clay can be exchanged with any group I (monocationic), group II (dicationic), group III (tricationic), alkali metal, alkaline earth metal or combination of groups I, II and III metal species and ions, and nano and micro sized particles form.

Organo-modified clay can be exchanged with any transition metal, late transition metal, lanthanide metal, heavy elements in ionic and nano and micro sized particles form.

Organo-modified clay can be exchanged with organic molecules including but not limited to pharmacological drugs, vitamins, and nutrients Some embodiments use clay sheets to provide controlled delivery of analgesic drugs to burn wounds while assisting in wound healing with its antimicrobial and moisture control properties.

Some embodiments use clay sheets to provide transdermal delivery of nutrients and pharmacological agents.

The disclosure provides a polymer-free organo-modified clay product. The organo-modified clay product has a clay and an organic compound. The organo-modified clay product is alternatively referred to in the disclosure as a film, a sheet, a mat or a membrane. The disclosed organo-modified clay product is referred to as polymer-free because polymer is not added for preparation of the clay product. The clay is montmorillonite, kaolinite, smectite, and bentonite. The organic compound is betaine, betaine hydrochloride, choline chloride, 3-Benzyl-5-(2-hydroxymethyl)-4-methylthiazolium chloride, 3-Benzyl-5-(2-hydroxymethyl)-4-methylthiazolium bromide, 3-Benzyl-5-(2-hydroxymethyl)-4-methylthiazolium fluoride or 3-Benzyl-5-(2-hydroxymethyl)-4-methylthiazolium iodide.

In some embodiments, a thickness of the polymer-free organo-modified clay product ranges from about 1 micrometer to about 500 micrometer. In some embodiments, a thickness of the polymer-free organo-modified clay product ranges from about 1 micrometer to about 100 micrometer. In some embodiments, a thickness of the polymer-free organo-modified clay product ranges from about 20 micrometer to about 60 micrometer. In some embodiments, a thickness of the polymer-free organo-modified clay product is about 50 micrometer.

In some embodiments, the polymer-free organo-modified clay product achieves a bending radius of curvature ranging from about 0.4 millimeter to about 10 centimeter. The bending radius of curvature is achieved without breaking the polymer-free organo-modified clay product. In some embodiments, the polymer-free organo-modified clay product achieves a bending radius of curvature ranging from about 0.3 millimeter to about 10 millimeter. In some embodiments, the polymer-free organo-modified clay product achieves a bending radius of curvature of about 0.5 millimeter. In some embodiments, the polymer-free organo-modified clay product achieves a bending radius of curvature of about 0.4 millimeter.

In some embodiments, the polymer-free organo-modified clay product has greater than 50% absorption of visible light. In some embodiments, the polymer-free organo-modified clay product is non-transparent. In some embodiments of the polymer-free organo-modified clay product, when the thickness of the product was about 50 micrometer, the film had greater than 50% absorption of visible light. In some embodiments, when the organo-modified clay product was further modified by addition of silver, the film absorbed greater than 82% of the visible light.

In some embodiments, the polymer-free organo-modified clay product does not incorporate a polymer. In some embodiments, the organo-modified clay product is a polymer free composite.

Antimicrobial Wound Dressing Application of Clay Sheets

The disclosed organo-modified clay materials stand out from the rest, as till date there is no available literature on synthesis of free-standing organo-modified or unmodified clay films that are prepared without using polymers or binders. Clay tends to swell when water is drawn into the interlayer space, allowing the cations to become easily exchangeable. In some embodiments, an N,N,N-trimethylglycine, also known as Betaine is intercalated into the clay. The hydroxyl groups of clay attach to the Betaine, expanding the clay. The silver ions in silver nitrate exchange with the sodium cations and take their place within the interstitial space as well. The silver ions in silver nitrate, the component added within the Montmorillonite gallery, is the main driving force for eliminating the microbes. Silver ions tend to have antiseptic properties used for controlling burn and eye infections. Silver ions have the ability to disrupt the bacterial cell wall, penetrate the cell and disrupt the physiological function of cell respiration and metabolites. In addition, silver is a bactericidal against more than 150 species of bacteria, viruses, yeast and fungi, including MRSA, MDR, *Klebsiella* and *Pseudomonas* species.

Water acts as an essential component in the antimicrobial bandage as well. Although most of it evaporates after the clay film is cast, some of it may remain within the clay film to provide moisture to the wound.

Organo-modified Silver-clay film can be used as an antimicrobial wound dressing. The bare clay and organo-modified clay films that can be used as burn and or wound bandages with membranes and adhesive patches can also be used to stop bleeding hence can be used as a hemostatic agent or bandage against wound bleeding and healing in 0-100 minutes time interval. The purpose of this product is to fulfill the function of a bandage as well as kill microbes, when applied to the wound. The product achieves its purpose of eliminating bacteria in less than 5 min-32 hour depending on the bacterial colony size.

Figure 1:
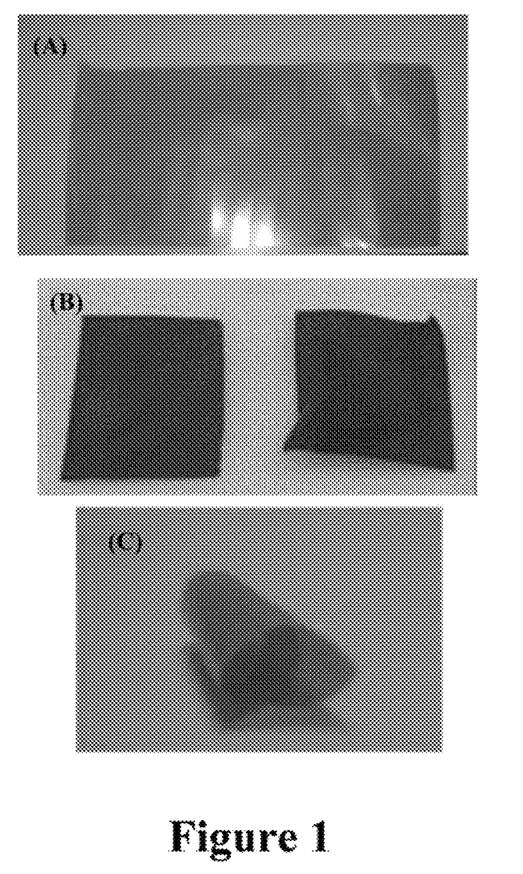
FIG. 1. (A) Photograph of the 12 cm width×8 cm height and 50 micrometer thick organomodified clay thin sheet product (B) Photograph of the 5 cm width×6 cm height and 30 micrometer thick silver exchanged organomodified clay thin sheet product (C) Photograph of the rolled-up clay sheet to demonstrate its flexibility and bend strength.

The bandages can be made available in three different film sizes ranging from 0.1 cm by 0.1 cm to 100 m by 100 m sizes (FIG. 1). These sizes are produced to cater to small, medium or large wounds. In some embodiments, the larger film products are also referred to as sheets. In some embodiments, if the size of the wound is small, a smaller size of the film product is cut and is referred to as a mat.

The silver clay sheet may also work effectively in eliminating other different types of microbes such as fungi or algae as well.

Silver-clay sheets serve multiple purposes in the burn and scar healing process. Clay has well-known property to retain moisture and has been used as a promoter for hemostasis. Clay with optimal silver concentrations can reduce the cost without compromising the efficacy of the silver.

There is a large amount of clinical evidence to support the use of hydrogel dressings in the treatment of hypertrophic scars. It may be due to the hydrogel dressing's ability to hydrate the damaged tissue, and allow oxygen to permeate to the surface of the skin. This will help in a localized increase in oxygen concentration leading to a down-regulation of signals that stimulate growth near the skin surface, thus preventing or reducing scar formation.

The final product was easily contoured as a bandage (strip or roll) with a silicone-based hydrogel adhesive. The bandage served as a burn and wound care product, which has huge commercial market for military and civilian casualties. The wound dressing can be applied to numerous applications, such as burn, wound and surgical care, and also in water filtration systems and for food packaging.

In some embodiments, the polymer-free organo-modified clay product includes an antimicrobial agent. The antimicrobial agent can be silver ion, copper, iodine, proflavine, silver-containing compounds, copper containing compounds, quarternary ammonium compounds, or quarternary phosphonium compounds. Silver-containing compounds include but not limited to silver sulfadiazine, silver nitrate, silver oxide, and silver carbonate; copper containing compounds include but not limited to copper oxide, copper sulfate, copper acetate, and copper nitrate; quarternary ammonium compounds include but not limited to benzalkonium alkyl chloride, cethyl trialkyl ammonium chloride, and alkyl dimethyl benzyl ammonium chloride and quarternary phosphonium compounds include but not limited to alkyl trimethyl phosphonium chloride and dialkyl dimethyl phosphonium bromide.

In some embodiments, the polymer-free organo-modified clay product includes an analgesic. The analgesic can be opioid analgesics, nonsteroidal anti-inflammatory drugs (NSAIDs) and adjuvant analgesics, capsaicin, clonidine, ketamine, Morphine, fentanyl, Buprenorphine or cannabinoids.

Some embodiments provide an antimicrobial dressing having the polymer-free organo-modified clay product. Some embodiments provide a burn wound dressing having the polymer-free organo-modified clay product.

Some embodiments provide a lithium battery having the polymer-free organo-modified clay product. The organo-modified clay product is the electrolyte membrane in the lithium battery.

Some embodiments provide a flame retardant product having the polymer-free organo-modified clay product. In some embodiments, the flame retardant product resists breakdown following acetylene flame for 2 minutes.

Some embodiments provide a method of antimicrobial treatment by administering the polymer-free organo-modified clay product.

Some embodiments provide a method of treating burns by administering the polymer-free organo-modified clay product.

A novel and successful approach to separate DMC from water and reaction products can be achieved by the clay sheets. The clay sheet can remove water from the organic chemical mixtures, efficiently. Nearly 100% of water can be removed from the mixture. This is an easier and energy conservative approach for separation of water from organic chemical mixture. Clay sheets are inert and will not react with organic compounds such as dimethyl carbonate and methanol, but clay absorbs water. Clay sheet will not get destroyed upon continuous application. Once saturated with water, the membrane can be heated to 50 degree C. to get rid of the water, and reused again for separation. Energy consumption is almost zero using this clay sheet compared to evaporation technique. Fast (<2-3 h) and Cost-effective technology compared to pervaporation approach and polymer based membranes used in the industry to separate water from organic chemicals.

Some embodiments provide a method of removing water from organic chemical mixtures using the polymer-free organo-modified clay product.

In flame retardant applications, by employing clay sheets in the outer shells, the thickness of Fire fighter's gloves can be reduced by up to 40 percent, permitting the improvement of hand function leading to better dexterity in difficult situations. Some embodiments provide a method of preparing a polymer-free organo-modified clay product. The method includes mixing a clay particle and an organo-containing solution to form a slurry. Then the slurry is casted on a substrate to obtain a slurry casted on a substrate. Then the slurry casted on the substrate is dried to obtain a dried product of the slurry on the substrate. Then the dried slurry product is separated from the substrate. The separated dried slurry product is the polymer-free organo-modified clay product. The polymer-free organo-modified clay product can be a film, a sheet, a mat or a membrane. In some embodiments, if the substrate is glass, then the dried slurry product has to be removed from glass substrate. In some embodiments, if the substrate is fabric or nylon, the dried slurry product need not be removed from the fabric or nylon. The resulting dried slurry product on the fabric or nylon substrate can together form part of a wound dressing product. Thus, dried slurry need not be removed from a nylon or fabric substrate. In this disclosed methods, no polymer has been added to the clay for preparing the product. In some embodiments of the method, the substrate can be a silicone sheet, a fabric or a glass surface. In some embodiments, the fabric is nylon. In some embodiments of the method when the product is prepared at a temperature of about 25 degrees C., the viscosity of the slurry prepared for spreading on the substrate ranges from about 2 centipoise to about 20 centipoise. In some embodiments of the method when the product is prepared at a temperature of about 25 C, the viscosity of the slurry prepared for spreading on the substrate ranges from about 5 centipoise to about 10 centipoise. In some embodiments drying the slurry casted on the substrate is performed under conditions of slow, air. In some embodiments drying the slurry casted on the substrate is performed at 20-25 degrees Centigrade under ambient, room temperature conditions.

Some embodiments provide a method of preparing a polymer-free organo-modified clay product. The method includes mixing a clay particle and an organo-containing solution to form a slurry. Then the slurry is casted on a substrate to form a slurry casted on a substrate product. Then the slurry casted on the substrate is dried to obtain the polymer-free organo-modified clay product. The organo-modified clay product can be a film, a sheet, a mat or a membrane.

Some embodiments provide a method of preparing a polymer-free organo-modified clay product having an antimicrobial agent. The method includes mixing a clay particle and an organo-containing solution. Then an antimicrobial agent containing solution is added to obtain a slurry. The slurry is casted onto a substrate. The casted slurry and substrate are subjected to drying and a dried slurry is obtained on the substrate. The dried slurry is separated from the substrate to obtain the organo-modified clay product containing the antimicrobial agent.

Some embodiments provide a method of preparing a polymer-free organo-modified clay product having an analgesic. The method includes mixing a clay particle and an organo-containing solution. Then an analgesic containing solution is added and a slurry is obtained. The slurry is casted on a substrate and dried to obtain a dried slurry on the substrate. The dried slurry is separated from the substrate to obtain the polymer-free organo-modified clay product having the analgesic compound.

Some embodiments provide an antimicrobial wound dressing. The wound dressing has a polymer-free organo-modified clay product having an antimicrobial agent. The wound dressing has successive layers of the following: a hydrogel adhesive with a hydrophobic backing; a polymer-free organo-modified clay product having an antimicrobial agent; and, a nylon membrane.

Some embodiments provide a method of preparing an antimicrobial wound dressing. The method includes successively layering the following: a hydrogel adhesive with a hydrophobic backing; a polymer-free organo-modified clay product having an antimicrobial agent; and, a nylon membrane. In some embodiments, the method includes successively layering the following: a nylon membrane, then a polymer-free organo-modified clay product having an antimicrobial agent; and, then a hydrogel adhesive with a hydrophobic backing.

Some embodiments provide an analgesic wound dressing. The analgesic wound dressing includes a polymer-free organo-modified clay product having an analgesic. The wound dressing has successive layers of the following: a hydrogel adhesive with a hydrophobic backing; a polymer-free organo-modified clay product having an analgesic and, a nylon membrane. Some embodiments provide a transdermal wound dressing. Some embodiments provide a method of preparing a transdermal wound dressing.

Some embodiments provide a method of preparing an analgesic wound dressing. The method includes successively layering the following: a hydrogel adhesive with a hydrophobic backing; then a polymer-free organo-modified clay product having an analgesic and, then a nylon membrane. Alternatively, the successive layering can be as follows: nylon membrane, then a polymer-free organo-modified clay product having an analgesic followed by a hydrogel adhesive with a hydrophobic backing.

It will be readily understood by the skilled artisan that numerous alterations may be made to the examples and instructions given herein. These and other objects and features of present invention will be made apparent from the following examples. The following examples as described are not intended to be construed as limiting the scope of the present invention.

EXAMPLES

Example 1

10 g sodium-exchanged montmorillonite clay (PGW) clay (Nanocor, Inc., Arlington Heights, Ill.), 190 g deionized water and 1.7 g anhydrous Betaine (Trimethylglycine) (Alfa Aesar, Ward Hill, Mass.) were added in a bottle and left to stir for 24 h. The resultant slurry was poured and spread on a glass plate with a large surface coverage. This allowed for formation of clay sheets with homogeneous thickness. Slurry was left to dry in air for 48 h on the glass plate at 20 to 25 degree C. After the slurry dried to form a clay sheet, the clay sheet was removed from the glass plate using a razor blade. The film thickness was varied from 1 μm to 500 μm by modifying the concentration and viscosity of the clay mixture and the spreading level of the slurry onto a surface. Photograph of some clay films are provided in FIG. 1A.

Example 2

Viscosity measurement of the clay slurry was performed to determine the viscosity required to optimize the flow ability of the clay slurry for the fabrication of clay sheets. Viscosity is the quantity that describes a fluid's resistance to flow and is heavily dependent on temperature. The viscosity of the slurry prepared in the example 1 was measured using a Brookfield DV-II+Pro Viscometer (Brookfield Instrument Laboratories Inc., Middleboro, Mass.) using a #42 spindle at 25-200 RPM speed. The measurement is carried out at temperatures of 23-25 degree C. In Table 1 viscosity of betaine-clay slurry as a function of spindle speed is provided.

TABLE 1

| Speed (rpm) | Viscosity (cP) |
|---|---|
| 25 | 7.94 |
| 50 | 5.95 |
| 75 | 3.97 |
| 100 | 3.97 |
| 125 | 3.18 |
| 150 | 2.65 |
| 175 | 2.27 |
| 200 | 2.48 |

The viscosity measurements showed that the consistency of the clay mixture before it was cast was similar to that of milk (about 8 cP at 25 degree C.). The viscosity of the slurry ranging from about 2 centipoise to 20 centipoise depending on the concentration of the clay in the mixture, yielded highly flowable slurry to form uniformly thick and mechanically durable clay sheets.

Example 3

10 g sodium-exchanged montmorillonite clay (PGW) clay, 190 g deionized water and 1.7 g anhydrous Betaine were added in a bottle and left to stir for 24 h. The resulting slurry was casted onto a silicone sheet. After drying the clay sheet was easily peeled off from the silicone tray surface.

Example 4

Preparation of Clay Film on Nylon Fabric 10 g sodium-exchanged montmorillonite clay (POW) clay, 190 g deionized water and 1.7 g anhydrous Betaine were added in a bottle and left to stir for 24 h. The slurry was casted onto a 12 inch×12 inch nylon fabric. Nylon fabric was cut into a smaller segment that was large enough to tightly wrap around a glass-casting sheet. Tape was used on the back to securely fasten the fabric onto the glass sheet. The clay slurry was then slowly poured out directly onto the fabric a doctor blade knife was then used to thin out and spread an even layer of clay on the fabric. The casted slurry was left to dry and was taken off as one piece with the nylon fabric.

Casting of clay on nylon fabric provided additional benefits compared to dry-casting of the clay alone. The added benefit was to shape and cut, or to even stitch pieces together gave us the option to create new shapes that might be needed with odd-shaped injuries located on areas such as the hands or feet.

Example 5

Preparation of Silver Ion-Exchanged Clay Sheets 10 g PGW clay, 190 g Deionized water and 1.734 g Betaine was combined in a capped plastic bottle and gently shook to initially combine all ingredients together into a slurry. A homogenizer was used to create a uniform viscosity mixture. The homogenization was continued until lumps of clay particles were no longer visibly settled at the bottom. Then the mixture was allowed to sit for 24 hours in a closed plastic bottle. 0.816 g silver nitrate (Alfa Aesar, Ward Hill, Mass.) was added to the clay slurry and homogenized again, the bottle was then wrapped in aluminum foil to prevent silver from being exposed to light and was left to sit for an additional 24 hours. Mixture was then washed and centrifuged to remove excess silver nitrate. Then the slurry was poured and casted on to glass plates, silicone trays and nylon fabrics.

It was critical to treat clay with betaine before ion-exchanging with silver nitrate. Reversing the order of preparation by first treating with silver ions and then treating with betaine resulted in poor quality silver clay sheets. Further, a silver clay film with higher betaine loading yielded a thicker and more flexible film that was both easier to remove from the glass sheet and was less susceptible to tearing for use. For example, 148 percent betaine exchanged clay yielded better silver clay sheets compared to 100 percent betaine exchanged clay. Photograph of the typical silver exchanged clay films are provided in FIG. 1B.

The first batch of the organo-clay film turned out to be very thick and did not flow smoothly onto the glass after it was cast. The film, after drying, felt very thick as well and since it didn't homogenize well, clumps could be observed. The film had a light shade of gray, unlike the dark gray or black that was expected. The film had many uneven areas, with some parts being very thin and some parts being very thick. It was easy to peel off the parts that were considerably thick. The reason for the clay film mixture being so thick was thought to be due to the fact that silver nitrate was added before the Betaine. The first batch was discarded because of all the problems mentioned above and a new batch was made with a modification in the procedure, which was the addition of Betaine before the silver. The purpose for this is so that the Betaine can intercalate within the interlayer first and then the silver can exchange with the cations, primarily sodium.

Additional water was also added to make the mixture easier to flow. The additional water had no effect on the concentration of the silver and most of it evaporated as the clay was drying.

After the change in procedure, the second batch turned out to be much smoother and flowed easily (similar to milk) onto the glass. There were no areas that were thinner or thicker than the rest. The color of the mixture as it was being cast was a peachy brown and the mixture spread on the glass by itself, as it was being poured. After 3 days of drying, the film was observed to be black in color towards the outside and lighter gray towards the inside. Since the film was appropriately thin, it was a bit difficult to initially start peeling it off from the glass but then it slid off easily. Circular rings of black and gray were also found on the film. These rings were observed on the other batches as well.

The occurrence of these rings was predicted to be because of how the mixture was being poured onto the glass plate. It was not being evenly spread, therefore some spots ended up with more material and some spots with less, causing the color variation. Although the rings had no effect on the antimicrobial testing (it still kills the bacteria), efforts were made to reduce the number of rings and produce a completely black film. The new batches of clay were poured very carefully and slowly in the center of the glass plate and allowed to spread by them. This technique seems to have worked and produced a considerably black film without many grayish areas or significant amount of rings.

The gray area is restricted in the middle unlike, where a lot more gray is observed. Also there is no brownish area in the middle either. Although a couple of rings can be observed, they are less in number compared to previous films.

Example 6

Clay Product Thicknesses

Thickness of the clay sheet prepared according to the Example 1 was measured using a micrometer. The average thickness obtained from the clay product samples was about 50 micrometer.

Example 7

Opacity of Clay Films and Silver-Clay Film

The optical absorption spectra of clay films was measured on a Beckman DU 530 UV-VIS Spectrophotometer using fixed wavelength (600 nm) mode. The percentage absorption of 600 nm wavelength light by the clay film having a thickness of about 50 micrometer was 56%. The percentage absorption by silver-clay film having a thickness of about 50 micrometer was 82%.

Example 8

The flexibility of the clay films was determined by measuring the maximum bending angle and the corresponding radius of curvature before breaking of the product. The bending angle was measured by mounting a rectangular clay specimen of size 2 inch by 2 inch and 50 micrometer thickness on a Mitutoyo No. 180-301B protractor head mounted to a Mitutoyo No. 180-703 steel rule. The measured angle of bending at the break of the clay sample was 36 degree. The radius of curvature derived from the bend angle at the break of the sample was about 0.5 mm. FIG. 1C provides a photograph of the clay film rolled up to show its flexibility.

Example 9

The bending angle at the break of a rectangular silver-clay specimen of size 2 inch by 2 inch and 30 micrometer thickness of the clay sample was 30 degree. The radius of curvature derived from the bend angle at break of the sample was about 0.4 mm.

Example 10

Antimicrobial Testing Clay Sheets and Silver Ion-Exchanged Clay Sheets

The efficacy of silver ion-exchanged clay sheet was tested using the antibacterial susceptibility test, (agar diffusion test) which utilizes the size and presence of the zone of inhibition to measure antimicrobial effectiveness. The testing process was carried out by spreading a thin layer of bacteria, grown in a growth medium, over the agar and then placing the circular cutouts of the clay film on top. The purpose was to determine the zone of bacterial growth inhibition around the pieces of film.

Typical gram negative and gram positive bacteria for a single test were *Escherichia coli, Staphylococcus epidermidis, Staphylococcus aureus* and *Bacillus subtilis*. Unmodified Clay sheets were used as control samples along with silver ion-exchanged clay sheets in the antimicrobial tests.

Figure 2:
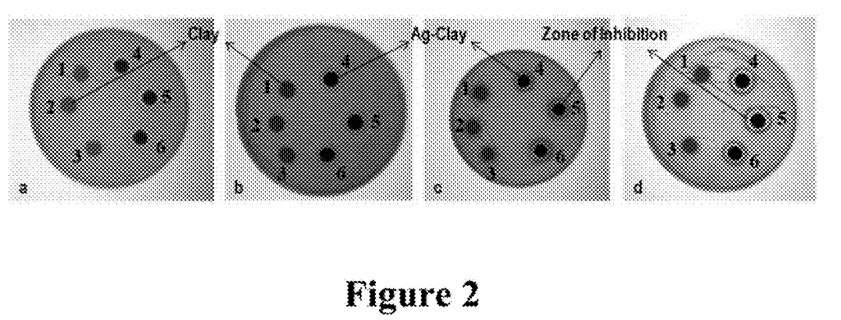
FIG. 2. Antimicrobial efficacy of organo-modified Ag-Clay films after 36 hours. Bacteria specimens (a) *Escherichia coli* (b) *Staphylococcus epidermidis* (c) *Bacillus subtilis* and (d) *Staphylococcus aureus* and cultured in petri dishes and tested at MMI. Distinct zones of inhibition from films (Ag-Betaine-Clay) compared to pristine Betaine-Clay films are to be noted. Betaine-clay film specimens are labeled as 1, 2 and 3 and silver-betain-clay film specimens are labeled as 4, 5 and 6.

Photographs showing the zone of inhibition for all 4 types of bacteria by Silver organo-modified clay film disks (labeled as 4, 5 and 6 in FIG. 2) along with control pristine clay film discs (labeled as 1, 2 and 3 in the FIG. 2) are provided in FIG. 2. The smallest zone was for *B. subtilis* and the largest was for *S. epidermidis*. In general, gram-positive bacteria are easier to kill and since *S. epidermidis* is a gram-positive bacterium, it could explain why the zone of inhibition for it is larger within the incubated time period (48 hours). The unmodified betaine-clay sheet control specimens did not exhibit a zone of bacterial growth inhibition.

The presence of the zone of inhibition showed that the silver successfully inhibited the growth of bacteria and that the clay film was suitable for use as an antiseptic.

Example 11

Methods and Materials

A. 0.4 wt % of Silver Containing Betaine-Clay Slurry 10 g PGW clay, 190 g Deionized water and 1.734 g Betaine was combined in a capped bottle and gently shook to initially combine all elements together into a slurry.

The homogenizer was then used to create a uniform viscosity throughout the mixture. It was used until lumps of clay were no longer visibly settled at the bottom.

The mixture was allowed to sit for 24 hours.

0.816 g AgNO3 was added in and homogenized again, the bottle was then wrapped in aluminum foil (to prevent the Ag from being exposed to light) and was left to sit for an additional 24 hours.

Mixture was then washed and centrifuged 3 times (should be 4 times but clay would not settle to be decanted properly)

Mixture is ready to be poured and casted on to Nylon fabric.

B. 0.4 wt % of Silver Containing Betaine-Clay Slurry 10 g PGW clay, 190 g Deionized water and 1.734 g Betaine was combined in a capped bottle and gently shook to initially combine all elements together into a slurry.

The homogenizer was then used to create a uniform viscosity throughout the mixture. It was used until lumps of clay were no longer visibly settled at the bottom.

The mixture was allowed to sit for 24 hours.

1.020 g AgNO3 was added in and homogenized again, the bottle was then wrapped in aluminum foil (to prevent the Ag from being exposed to light) and was left to sit for an additional 24 hours.

Mixture was washed, decanted and centrifuged 4 times.

Mixture is ready to be poured and casted on to Nylon fabric.

Casting on to Nylon Fabric:

Nylon fabric was cut into a smaller segment that was large enough to tightly wrap around a glass-casting sheet. Tape was used on the back to securely fasten the fabric onto the glass sheet.

Ag clay was then slowly poured out directly onto the fabric (mixture was very thick and sat upon the fabric rather than soaking in) a microscope slide was then used in an attempt to thin out and spread an even layer of clay upon the fabric.

Cast was left to dry and was taken off as one piece with the Nylon fabric.

Nylon clay film was then rolled on to a dowel.

Anti-Bacterial Efficacy of Silver-Clay Nylon Fabric

This experiment was to test the efficacy of anti-bacterial Nylon fabric samples from 0.4 wt % silver slurry, nylon fabric samples from 0.5 wt % silver slurry and untreated nylon fabric was used as a control.

*Bacillis subtilis* was the bacteria type used for testing; pre-made 1 mL of growth media was dropped onto hardened agar using a micro pipette. The bacterium was then spread evenly in the Petri-dish upon the agar using a UV-sterilized rubber policeman.

Two punch outs were made with each type of test material. All instruments and both sides of each material were sterilized using UV light and placed on to the agar containing *B. subtilis*. Two Petri-dishes containing 2 types of each material were made for comparison. All two finished Petri-dishes were then placed in the incubator at 37 degree C.

Figure 3:
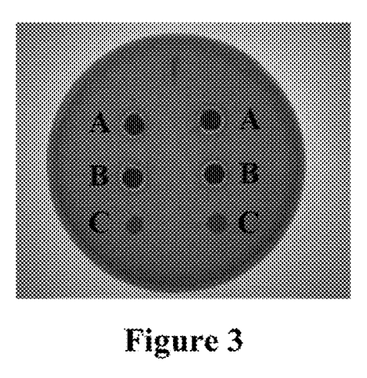
FIG. 3. Antimicrobial efficacy of organo-modified silver-Clay films after 24 hours. A. Nylon fabric prepared using 0.5 wt % silver containing silver-betaine-clay slurry: B. Nylon fabric prepared using 0.4 wt % silver containing silver-betaine-clay slurry C Untreated Nylon fabric FIG. 4. Schematic layered structure of antimicrobial burn wound dressing.
Figure 4:
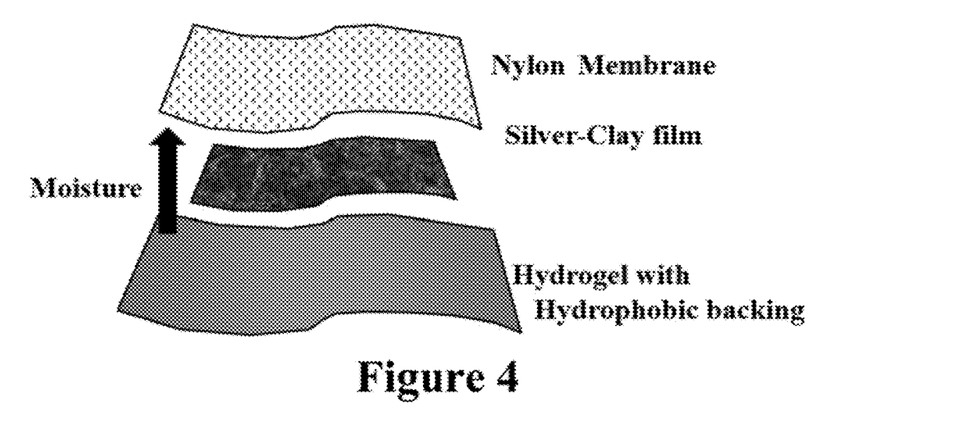

Zones of Inhibition can be clearly noted by the distinctive halo-like effect around the Silver Clay Nylon punch outs, both on the 0.4 wt % silver (labeled as A in the FIG. 3) and 0.5 wt % silver (labeled as B in the FIG. 3) t concentrations. There was no zone of inhibition observed for control uncoated-nylon fabric sample (labeled as C in the FIG. 3).

Example 12

Water Vapor Transmission Rate (WVTR) Testing for Silver Clay Sheets on Nylon Cloth Historically it was believed that wet wound environments would introduce a wound to increased risk factors related to bacteria and infection. However, there is increasing amounts of evidence that wound healing takes place most rapidly in clean, moist environments. Researchers have stated that a low WVTR is a dependable indication of the dressing's ability to retain moisture and thus create a moist, ideal environment that promotes rapid healing.

WVTR values were measured to determine the moisture retention ability of the Nylon-Cast silver clay sheet. The moisture permeability of the silver clay sheet was determined by measuring the water vapor transmission rate (WVTR) across the material as stipulated by a modified ASTM standard method E96. The test involved mounting a disc of the test material in a specially designed vial containing water. The material was positioned across the opening of the cup, in a desiccator at 35 degree C. and with relative humidity maintained at 15 to 20 percent. The weight of the water filled vial with the test material was measured at hourly intervals to calculate the amount of water loss per hour.

Dressings with WVTR values less than 35 g per square meter per hour can be defined as moisture retentive. Typical WVTR values observed for silver organo-modified clay sheets were 16 to 36 g per square meter per hour depending on the thickness and amount of silver present in the clay sheet.

Example 13

Burn Wound Dressing Fabrication Incorporating Silver Clay Sheet

A prototype burn bandage was developed by successive layering of (a) Nylon membrane (b) silver clay sheets and (c) hydrogel adhesive. Typical Dimensions were as follows. Silver clay sheet: 1.5 inch by 2.4 inch; Delnet Membrane: 2 inch by 3 inch; Hydrogel sheet: 3 inch by 4 inch; Cover slip: either cut to the size of the hydrogel or cut to 3 inch by 5.5 inch. Schematic diagram of the antimicrobial burn wound dressing is provided in FIG. 3.

The nylon membrane serves as a porous membrane to control moisture flow to the organo-modified silver clay film, while at the same keeping the film and place and preventing particles from the film breaking off into the wound.

Clay sheet acted as a moderator layer between the wound surface and hydrogel.

The hydrogel bandage provided both adhesive to hold the bandage in place and a soothing cooling sensation beneficial for burn care. The hydrogel was also a water reservoir to keep the wound surface moist.

The multilayer wound dressing was packaged in heat-sealable foil pouches.

The final product was easily contoured as a bandage (strip or roll) with a silicone-based hydrogel adhesive.

Example 14

In-Vivo Testing of Silver Clay Sheet Wound Dressing

Silver clay sheet antimicrobial wound dressing was evaluated using animal burn wound models. Wound dressing was prepared as in Example 13. Two Yorkshire cross pigs were randomized to three treatment protocols after full thickness burns were created. Contact burns were created paravertebral under aseptic conditions. A Rhinhart Electric Dehorner was heated to a maximum temperature of 1,000 degree F. and was placed on the dorsum of the animal until the proper depth of 1 cm was reached (typically 10 seconds). A total of six burn sites, each 11 square centimeter was created on the dorsum of the animal with 4-5 cm between each site.

Figure 5:
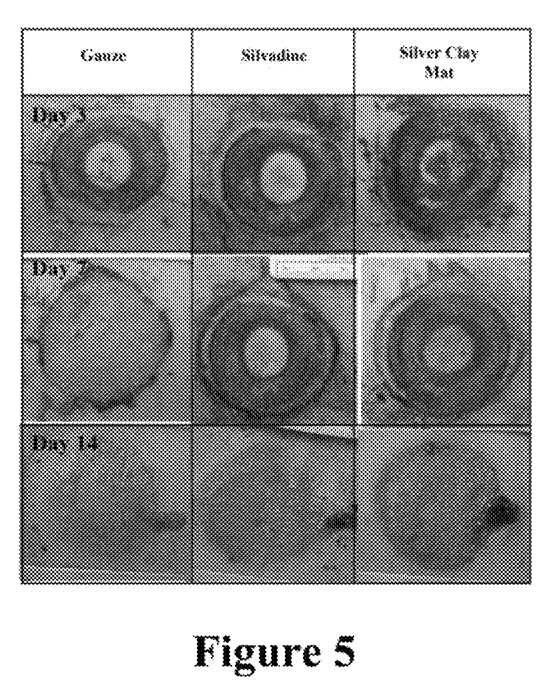
FIG. 5. Photographs showing progress in burn wound healing with gauze (negative control), Silvadine cream (positive control) and silver exchanged clay burn wound bandage.

The wound received three treatment protocols, namely Gauze, silvadine cream and silver clay sheet dressing. Silver clay wound dressing was prepared as described in the Example 13. Dressings were changed 3 times a week for the first 14 days for the gauze and silvadine cream treatments. The silver clay sheet dressing was changed only every 7 days. Photographs showing the wound healing progress is provided in FIG. 5.

Sites treated with silver clay sheet (or mat) dressing required less daily care and dressing changes as compared to the other two treatments unmedicated gauze and silvadine cream for the first 10 days. Time to full granulation for each group was 14 days. In summary, silver clay sheet dressing demonstrated similar healing activity with that of Silvadene® cream, albeit with significantly less wound care and number of dressing changes.

Example 15

The application of clay sheets as transdermal delivery patches were evaluated by measuring the uptake and release of organic dyes by the clay sheets. A clay sheet similar to the one described in the Example 1 as dipped in methylene blue dye solution in water. 10 g sodium-exchanged montmorillonite clay (PGW) clay, 190 g deionized water and 1.7 g anhydrous Betaine were added in a bottle and left to stir for 24 h. The slurry was casted onto a silicone sheet. After drying the clay sheet was easily peeled off from the tray surface. Then a 2 inch by 2 inch sheet was cut from the dried clay sheet and dipped in methylene blue dye solution in water. After 5 minutes the clay sheet was taken out of the methylene blue solution. The color of the clay sheet turned from yellowish brown to dark blue due to the uptake of the organic dye. This demonstrates that organic chemicals such as drugs could be loaded onto a clay sheet and used as transdermal patches for drug delivery. After 5 minutes the clay sheet was taken out of the methylene blue solution. The color of the clay sheet turned from yellowish brown to dark blue due to the uptake of the organic dye. This change in color was similar to loading of drugs to a patch.

The dye loaded-clay sheet was then placed in a phosphate buffer solution. The dye was slowly released into the solution with the clay sheet intact. This experiment showed that the clay sheets could be used in preparing a drug delivery patch.

Example 16

Clay sheets as prepared in the Example 1 were used as fire-resistant sheet. Clay sheet are a safe-alternative to asbestos because clay sheet are inorganic materials similar to asbestos but without the harmful side effects.

5 g sodium-exchanged montmorillonite clay (PGW) clay, 190 g deionized water and 0.9 g anhydrous Betaine were added in a bottle and left to stir for 24 h. The slurry was casted onto a silicone sheet. After drying the clay sheet was easily peeled off from the tray surface. The thickness of the dried clay sheet was 0.2 mm. This sheet was used in flame penetration tests.

Figure 6:
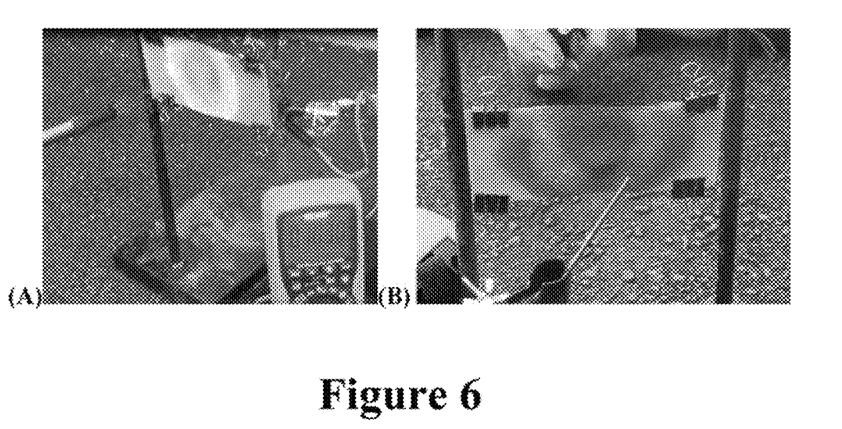
FIG. 6. Photograph of heat resistant test conducted on clay samples (A) Fire side and (B) Sample is intact after 2 min of exposure to acetylene gas flame.

Flame penetration tests were conducted on thin clay fabrics (0.2 mm thick). Horizontal and vertical flame burn tests were conducted on several candidate sheets. Clay sheets were found to be immediately self-extinguishing. Burn damage on the clay sheet was confined locally to the heated zone beneath and around the lit torch tip's flame. All flames were immediately self-extinguishing beyond those regions, with zero after flame times recorded. The clay fabric exhibited a rise in back-side temperature less than 10 degree F. after 20 second flame exposure. Photographs of the fire retardant tested samples are provided in FIG. 6.

Example 17

Application of Clay Sheets as a Membrane for Separating Organic Molecule from a Mixture Clay sheet produced as in the example 1 were tested for use as a membrane for separation technologies, such as Dimethyl carbonate-Methanol-water under ambient conditions.

Betaine-Clay membrane submerged in DMC per Methanol per Water Solution:

30 mL Dimethyl Carbonate, 60 mL Methanol and 5 mL of distilled water were mixed together in a 500 mL beaker. 3 such mixtures were in separate beakers Two clay sheets were cut into rectangle sheets of size 4.5 inch×2.25 inch and were placed in the dimethyl carbonate/methanol/water mixture solution for 2 h. Then the beakers were left undisturbed for 2 h and resulting clay sheets and solutions were weighed.

Clay Sheet 1

Thickness of the clay sheet 30.48 micron

Weight of the clay sheet before dipping in test solution 0.5574 g

Weight of the clay sheet after dipping in test solution 0.8854 g

Increase in weight due to water absorption 0.3280 g

Clay Sheet 2

Thickness of the clay sheet 99.60 micron

Weight of the clay sheet before dipping in test solution 1.3217 g

Weight of the clay sheet after dipping in test solution 1.7080 g

Increase in weight due to water absorption 0.3863 g

The increase in weight clearly demonstrate the efficiency of water removal from organic mixtures by the clay sheets.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A polymer-free organo-modified free-standing antimicrobial transdermal clay film comprising a clay, a zwitter ion, and an antimicrobial agent, wherein the antimicrobial agent is selected from a group consisting of silver ion and silver-containing compounds, wherein the zwitter ion is selected from the group consisting of N,N,N-trimethylglycine and N,N,N-trimethylglycine hydrochloride, wherein the silver-containing compounds are selected from the group consisting of silver nitrate, silver oxide, and silver carbonate, and wherein the polymer-free organo-modified free-standing antimicrobial transdermal clay film is used for transdermal application.

2. The polymer-free organo-modified free-standing antimicrobial transdermal clay film of claim 1, wherein the clay is selected from the group consisting of montmorillonite, kaolinite, smectite, and bentonite.

3. The polymer-free organo-modified free-standing antimicrobial transdermal clay film of claim 1, wherein a thickness of the polymer-free organo-modified free-standing clay film ranges from about 1 micrometer to about 500 micrometer.

4. The polymer-free organo-modified free-standing antimicrobial transdermal clay film of claim 1, wherein a thickness of the polymer-free organo-modified free-standing clay film ranges from about 1 micrometer to about 100 micrometer.

5. The polymer-free organo-modified free-standing antimicrobial transdermal clay film of claim 1, wherein the polymer-free organo-modified free-standing clay film achieves a bending radius of curvature ranging from about 0.4 millimeter to about 10 centimeter.

6. The polymer-free organo-modified free-standing antimicrobial transdermal clay film of claim 1, wherein the polymer-free organo-modified free-standing clay film has greater than 50% absorption of visible light.

7. The polymer-free organo-modified free-standing antimicrobial transdermal clay film of claim 1 further comprising an analgesic.

8. The polymer-free organo-modified free-standing antimicrobial transdermal clay film of claim 7, wherein the analgesic is selected from the group consisting of opioid analgesics, nonsteroidal anti-inflammatory drugs (NSAIDs) and adjuvant analgesics, capsaicin, clonidine, ketamine, Morphine, fentanyl, Buprenorphine and cannabinoids.

9. An antimicrobial dressing comprising the polymer-free organo-modified free-standing antimicrobial transdermal clay film of claim 1.

10. A burn wound dressing comprising the polymer-free organo-modified free-standing antimicrobial transdermal clay film of claim 7.

11. A polymer-free organo-modified free-standing antimicrobial transdermal clay film prepared by a method, the method comprising:
（a) mixing a clay particle and a zwitter ion solution to form a slurry;
(b) adding an antimicrobial agent to the slurry of step (a) to form a second slurry;
(c) casting the second slurry of step (b) on a substrate to form a third slurry casted on a substrate;
(d) drying the third slurry casted on the substrate of step (c) to obtain a dried product; (e) separating the dried product of step (d) to obtain the polymer-free organo-modified free-standing antimicrobial transdermal clay film, wherein the antimicrobial agent is selected from a group consisting of silver ion and silver-containing compounds, wherein the zwitter ion is selected from the group consisting of N,N,N-trimethylglycine and N,N,N-trimethylglycine hydrochloride, wherein the silver-containing compounds are selected from the group consisting of silver nitrate, silver oxide, and silver carbonate, and wherein the polymer-free organo-modified free-standing antimicrobial transdermal clay film is used for transdermal application.

* * * * *